United States Patent [19]

Rhodes et al.

[11] Patent Number: 5,837,896
[45] Date of Patent: Nov. 17, 1998

[54] DETECTION OF DEFECTS USING RESONANT ULTRASOUND SPECTROSCOPY AT PREDICTED HIGH ORDER MODES

[75] Inventors: George Rhodes; James J. Schwarz, both of Albuquerque; David E. Thomas, Peralta; Ming Lei, Albuquerque, all of N. Mex.

[73] Assignee: Quasar International, Albuquerque, N. Mex.

[21] Appl. No.: 520,009

[22] Filed: Aug. 23, 1995

[51] Int. Cl.⁶ .................................................. G01N 29/12
[52] U.S. Cl. ............................................................ 73/579
[58] Field of Search .......................... 73/579, 602, 659; 364/560, 563

[56] References Cited

U.S. PATENT DOCUMENTS

| | | |
|---|---|---|
| 4,446,733 | 5/1984 | Okubo ........................................ 73/579 |
| 4,926,691 | 5/1990 | Franklin et a. ............................ 73/579 |
| 5,425,272 | 6/1995 | Rhodes et al. ............................ 73/579 |
| 5,571,966 | 11/1996 | Tsuboi ....................................... 73/579 |

*Primary Examiner*—Michael Brock
*Assistant Examiner*—Nashmiya Fayyaz
*Attorney, Agent, or Firm*—Ronald R. Snider

[57] ABSTRACT

Methods for the prediction of the frequency of high order resonant ultrasound spectroscopy (RUS) diagnostic modes are used to limit the band width of diagnostic testing at high order mode frequencies. Testing of parts at low order frequency modes is used to calculate part dimensions, and then these calculated part dimensions are used to predict high order diagnostic mode frequencies. Lower order mode frequencies are used to predict high order diagnostic mode frequencies.

13 Claims, 7 Drawing Sheets

DETECTION OF DEFECTS USING RESONANT ULTRASOUND SPECTROSCOPY AT PREDICTED HIGH ORDER MODES

BACKGROUND

1. Field of the Invention

This invention is in the field of nondestructive testing by use of a resonant ultrasound spectroscopy (RUS). RUS is to be distinguished from ultrasonic testing in that it subjects an object to ultrasonic vibrations and which detects ultrasonic vibrations emitted at a natural frequency of the object.

The term RUS (resonant ultrasound spectroscopy) is defined as: an application of a continuous sweep of frequencies as shown in U.S. Pat. No. 4,976,148 or in steps as shown in U.S. Pat. No. 5,408,880, and the measurement is observation of the response of the object to the frequency which is applied.

2. Prior Art

The art of resonant ultrasound spectroscopy has been developed as previously disclosed in U.S. Pat. Nos. 4,976,148; 5,408,880: 5,355,731; 5,062,296; and 5,425,272. Each of these patents is incorporated herein by reference.

In addition, the Assignee of this application has filed a U.S. patent application Ser. No. 08/075,159 now U.S. Pat. No. 5,495,763 filed Jun. 10, 1993 entitled "Method for Resonant Measurement" and U.S. patent application Ser. No. 08/409,218, now U.S. Pat. No. 5,631,423 filed Mar. 23, 1995 entitled "Method for Resonant Measurement" which cover further improvements in the RUS technology. These pending applications are also incorporated herein by reference.

Resonant Inspection using Resonant Ultrasound Spectroscopy (RUS) uses higher order modes (high frequencies) to detect small defects. RI does this by transmitting CW energy to the object. The frequency is swept across the frequency range of interest. The part vibrates when the drive matches the frequency of one of its characteristic modes. Each mode is measured independently and RI uses sensitive receivers, to accurately measure hundreds of modes. As a result, RI can measure very small defects (or small changes in dimensions).

There are major differences among other prior art techniques in how the energy is used to detect defects. Prior art systems include ultrasonic time of flight, ultrasonic imaging, and use of impulse vibrations. Each of these are discussed below.

Ultrasonic Time of Flight is essentially an acoustical radar (more properly, a sonar). A pulse of acoustical energy is transmitted into the object being tested. The pulse travels through the object until it reaches a discontinuity, such as the other side of the object or a flaw within the object. The discontinuity reflects the pulse and the return (echo) is sensed. The time between the transmission of the pulse and its return, is proportional to the distance to the discontinuity. Application of this technique to a wall as the transmitter/receiver moves along the wall, can be effective for sensing the thickness of the wall, and can present a profile of the wall thickness. The technique is referred to by those in the art as ultrasonic because the pulse widths must be short compared to the propagation time, which corresponds to frequencies beyond human hearing (>20 kHz).

Ultrasonic Imaging is where the receiver is placed on the other side of the object from the transmitter, that is opposite the transmitter. If the setup is such that the reflections off the surfaces can be ignored, and the transmitter and receiver are scanned in step, across the surface, then the signal obtained by receiver is an outline (image) of the discontinuity. Again practical considerations require that ultrasonic frequencies be used.

Impulse Vibrations applies a pulse of acoustical energy, usually by striking a sharp blow to an object. This approximates a mathematical impulse function, so the response is the transfer function of the object. In response, the object vibrates in the form of a damped sinusoid which contains all of the frequencies in the transfer function, that is all of the object's vibrational modes. If a defect is present the modes should be effected. It is difficult to obtain any useful information about defects directly from the damped sinusoid. Usually, this time domain wave form is transformed to the frequency domain using a Fourier Transform. However, the amplitude of the sinusoid is dominated by the amplitude of the first resonant mode and the process is inherently noisy, so only the first few modes can be accurately computed. This is sometimes enough to detect large defects, but not small defects.

BRIEF SUMMARY OF THE INVENTION

This invention utilizes resonant ultrasound spectroscopy (RUS). RUS can be generated in accordance with the teachings of U.S. Pat. No. 5,425,272 and U.S. Pat. No. 5,408,880. These patents, in FIGS. 1, 2, and 3 in the accompanying descriptions, teach one skilled in the art how to generate RUS in accordance with this invention.

The term RUS refers to the application to an object of acoustic waves having different frequencies within a predetermined frequency range wherein the step of applying the acoustic waves involves defining a response time interval which depends on the elastic properties of the material, defining a frequency step interval, sweeping the acoustic wave frequency at step intervals through the predetermined frequency range, and where each frequency is applied during the defined small response time interval. This invention is an improvement in analysis of the detected response of an object to the application of RUS. Object responses to RUS can be classified as response modes, i.e., a response where the part exhibits a resonant response to the applied vibrations. Low order modes as used in this application refers to modes where the frequency is low (within the first few resonances, such as 20), and high order modes refers to modes where the frequency is considered high (that is, where there are many closely spaced modes). Parts exhibit response peaks where the part resonates and produces a detectable vibration which is converted into an electrical signal. The magnitude of the converted electrical signal is proportional to the part resonance. Observation of part resonances leads to powerful tools used to analyze parts during nondestructive testing.

As shown in the prior art, it has been observed that splitting of resonant modes (see U.S. patent application Ser. No. 08/075,159 now U.S. Pat. No. 5,495,763 filed Jun. 10, 1993 entitled Method for Resonant Measurement, incorporated herein by reference), and observing the distance between resonant modes (see U.S. Pat. No. 5,425,272) provide important information as to whether a part is good or bad.

The reason for measurement at higher order modes is so that part defects which are smaller, such as very small cracks, or other small defects, can be detected. The problem with high order mode testing is that in the higher order modes, there are many part responses which clutter response spectrum and make it difficult to identify specific high order mode responses which may be buried within the spectrum. Next, as a practical matter, speed of measurement can be substantially increased if one knows where to look for the high order resonant modes. This allows the use of a narrower frequency band for the high order mode testing by RUS. In this invention, applicant has provided improvements in RUS parameter measurement which lead to even more powerful methods for determining whether a part is good or bad. In this invention, applicant teaches a method of measurement wherein the resonant responses at low order modes is used to predict resonant response at higher order modes. The prediction of high order mode resonant response allows the use of a narrow frequency band for the high order resonant test, thereby eliminating unnecessary testing and consequent time consumption scanning frequencies where there is no meaningful response.

Previous work has shown the feasibility of detecting defects in manufactured parts using Resonant Ultrasound Spectroscopy (RUS). The defects are detected by observing either splits in a degenerate mode or shifts in a non-degenerate mode. These techniques detect either cracks or non-homogenieties (such as chips, voids, inclusions, asymmetry or asphericity). However, there is a practical limit on the minimum size of defect that can be detected in a given part. This minimum size is determined by two parameters, the Q of the material (the material's mechanical lossiness) and the size of the defect relative to the size of the part itself. There is no known way to extend the detection limit beyond the limit set by the material Q. The approach of this invention is to use higher frequencies, i.e., higher order modes. Detection of smaller defects requires shorter wavelengths and thus higher frequencies. Unfortunately, as the frequency is increased for a given part, the mode density (i.e., the number of modes per frequency window) increases. Each of these modes also moves relative to its neighbors as the dimensions vary across a production run. As a result, when the frequency exceeds about ten times the frequency of the first resonance, it becomes unfeasible to track a specific mode to determine whether it split or shifted. This is not a problem with other resonant test techniques, because they cannot measure beyond the first few modes. However, RUS can measure literally hundreds of modes so a technique is needed to use these high order modes to detect small defects, despite the mode saturation. The use of a narrow frequency band is possible because the location of a high order resonant mode is predicted in advance by the methods of this invention.

In the first embodiment of the method of this invention, an object is measured by RUS at low order modes, then higher order mode frequencies are computed based upon the measured low order modes, and then measurement of the object by diagnostic RUS at the higher order mode frequencies where responses are predicted is completed.

In another embodiment of this invention, the use of RUS is combined with a surface acoustic wave measurement (SAW) in order to predict high order surface acoustic wave modes. SAW is disclosed in U.S. Pat. No. 5,355,731. In this method, frequencies for selected low order modes are first computed based upon part geometry, and the measurement at low order modes is made. Next, there is comparison of the computed and measured frequencies from the selected low order modes of the object. From this comparison, dimensions of the object are determined. Once the object dimensions are determined, then expected higher order diagnostic modes can be computed from the dimensions of the objects utilizing the algorithms originally used for computing frequencies at low order modes and, finally, RUS measurement can be made at higher order frequency modes.

In another embodiment of this invention, applicant provides a method for the relationship between resonant frequency, specific response, density of an object where the density is not known. In this method, the basic relationships are first determined. Next, measurement by RUS and the object at at least two lower order modes is performed. A comparison between the difference between the frequency at the lower order modes then becomes independent of the part density because the part density function remains constant and is subtracted out. Once the dimension constants are obtained from the part, then higher order modes can be predicted, even though part density has not been determined.

In another embodiment of this invention, a plurality of parts known to not have any defects is first measured by RUS to determine low order resonant mode(s). Next, relationships between a resonant frequency mode, a specific resonant mode response, and dimensions of a part are determined. Based upon this information, expected frequencies of a high frequency resonant mode are predicted by calculating coefficients of the relationships from the measurements of frequency at low order frequency modes. Measurement of an unknown part at high order frequency modes by RUS can then proceed with a narrow band width of applied RUS, and the part can be accepted or rejected based upon a criterion applied to measured RUS response at the high order mode.

Often, measurement of the density of an object is not easily accomplished. Therefore, in accordance with this invention, applicant has developed a method of RUS measurement of an object whereby the density can be ignored, or where the density need not be known. This method involves determining relationships between the resonant frequency, specific response, and density of the object. Note, the density of the object affects the resonant frequency in accordance with the inverse square root of the density factor. An object is then measured by RUS at at least two low order modes, where the low order modes are dependent upon the same dimension and part density. In these two measurements, when the difference in measurements is determined, the density factor will be subtracted out. Next, measurement of two known good parts by RUS is made in order to develop independent equations for determining dimensioned constants for the expression of the difference in frequency.

DETAILED DESCRIPTION

This disclosure describes techniques for computing the expected frequency of a specific high order diagnostic mode, based on the measured frequency of related low order modes. The expected frequency is defined as the frequency at which a given resonance would occur if there was no defect in the part. The measurement can then be limited to the immediate vicinity of the expected frequency so that extraneous modes do not interfere with the measurement and the previously mentioned splits and shifts can then be used to detect the presence of any defect.

The resonant frequency of a particular mode in a good part is determined by several parameters. These include the elastic constants of the material, the material density and the dimensions. The elastic constants of the material are just that, constant. They do not vary, so they can be ignored for a given part. The density may vary from batch to batch, but is constant across a specific production run. The dimensions vary from part to part within a production run depending on the tolerances in the production process.

The dimensional variations constitute the primary limitation of detecting small defects. For simple shapes, the relationship between resonant frequencies and dimensions can be calculated from first principles. However, these relationships are too complex for use in a production environment. Experiments have shown that over the small range in variations encountered in a typical production run simple mathematical approximations can effectively describe the relationship between the frequency of a specific resonance $f_n$ and the dimensions of the part.

EXAMPLE 1

For a solid cylinder, the relationship between resonant frequency and dimensions for a particular mode can be approximated by:

$$f_n = A_n * L + B_n * D + C_n \tag{1}$$

where, $f_n$ is the frequency of the n-th resonance and "L" and "D" are the length and diameter respectively of the cylinder. The constants A, B and C are specific to each resonant mode, but apply to all parts of this type. For a more complex shape, a term must be included in the equation for each dimension (e.g., a hollow cylinder or a rectangular parallelepiped each requires four terms).

The constants A, B and C can be determined for mode "n" by measuring three parts "p", "q" and "r" and solving the simultaneous equations.

$$f_{np} = A_n * L_p + B_n * D_p + C_n \tag{2}$$

$$f_{nq} = A_n * L_q + B_n * D_q + C_n \tag{3}$$

$$f_{nr} = A_n * L_r + B_n * D_r + C_n \tag{4}$$

This by itself is not useful for sorting parts because in a production environment, the dimensions are generally not precisely known. However, for a specific part, the dimensions are fixed, so L and D are constant and A, B and C can be treated as variables. Using three modes "m", "n" and "o", equations 2, 3 and 4 can now be written as:

$$f_m = A_m * L + B_m * D + C_m \tag{5}$$

$$f_n = A_n * L + B_n * D + C_n \tag{6}$$

$$f_o = A_o * L + B_o * D + C_o \tag{7}$$

These equations can be solved for L and D, so that the dimensions can be expressed in terms of the frequencies $f_m$, $f_n$, and $f_o$ and of terms that include the A, B and C constants for the three modes. To minimize the number of terms in the equations, set up new constants U through Z, such that:

$$L = U * f_m + V * f_n W * f_o \tag{8}$$

$$D = X * f_m + Y * f_n Z * f_o \tag{9}$$

The relationship between the new constants and the previous constants can be solved with simple algebra, but that is not important to this discussion.

This information provides the basis for computing the estimated frequency for a high order mode $f_h$. Using equation 1, $f_h$ can be written:

$$f_h = A_h * L + B_h * D + C_h \tag{10}$$

equations 8 and 9 provide values for L and D. Substituting another set of constants R, S and T allows equation 10 to be rewritten:

$$f_h = R_h * f_m + S_h * f_n + T_h * f_o \tag{11}$$

The important result is the development of a theoretical basis for calculating the expected frequency of the high order mode as a function of low order modes. The application of this approach is limited to the range in which the simplified equations apply, but this has been shown to be adequate for the dimensional variations associated with typical manufacturing tolerances.

EXAMPLE 2

In practical application to RUS defect detection, it is not important to make any of the calculations described in the preceding section. The experimental procedure is to define the number "x", of variable dimensions for the part of interest. At least x+1 good parts are needed (for the x dimensional variables plus a constant term) whose dimensions vary over the range of interest. For each part x+1 low order modes are measured plus the high order mode of interest. An equation of the form of equation 11 is solved for the x+1 constants. Then, these constants can be used with the measured low order modes to compute the expected frequency of the high order mode for any part of this type. This approach has been found to predict the expected frequency with an accuracy better than 99%.

If the high order mode has been previously determined to be diagnostic for defect detection, the appropriate RUS defect detection algorithm can be applied. An alternative approach is to use more parts and use a standard best fit technique to fit equation 11 to the data. This can be particularly valuable if exogenous variables (such as the quality of the part or its density) are present.

Figure 1A:
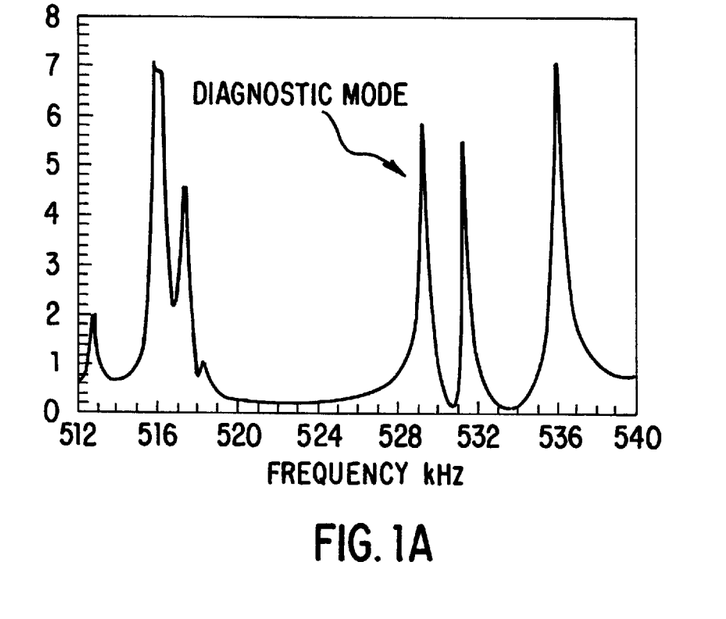
FIG. 1a shows the spectrum for a small part in the vicinity of the diagnostic mode for a part which is smaller than normal.
Figure 1B:
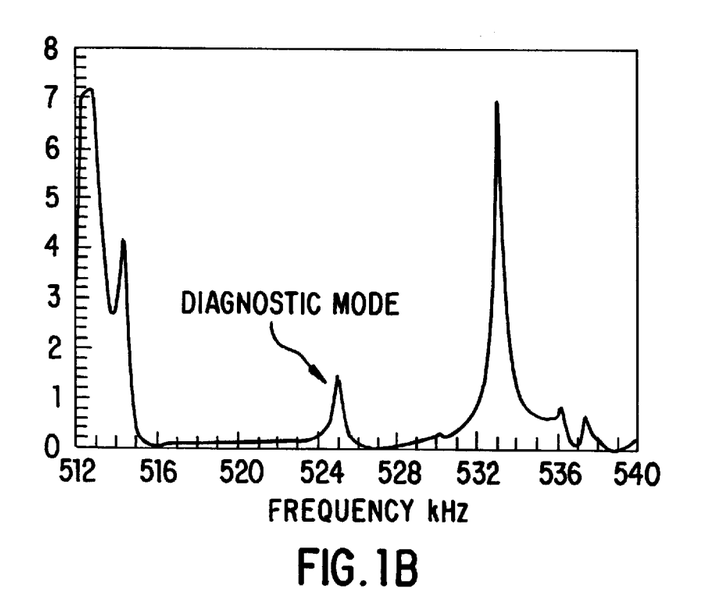
FIG. 1b shows the same spectral window for a part which is larger than normal.

RUS testing has previously identified the splitting of the labeled mode to be diagnostic of a defect of interest. FIG. 1a shows the spectrum for a small part (that is, within tolerances, but smaller than the mean) in the vicinity of the diagnostic mode. FIG. 1b shows the same spectral window for a large part. Both parts are within the acceptable manufacturing tolerance. Clearly, it would be difficult for a computer (or an operator) to consistently identify the small diagnostic mode in the presence of the other modes.

Figures 2A, 2A, 2A:
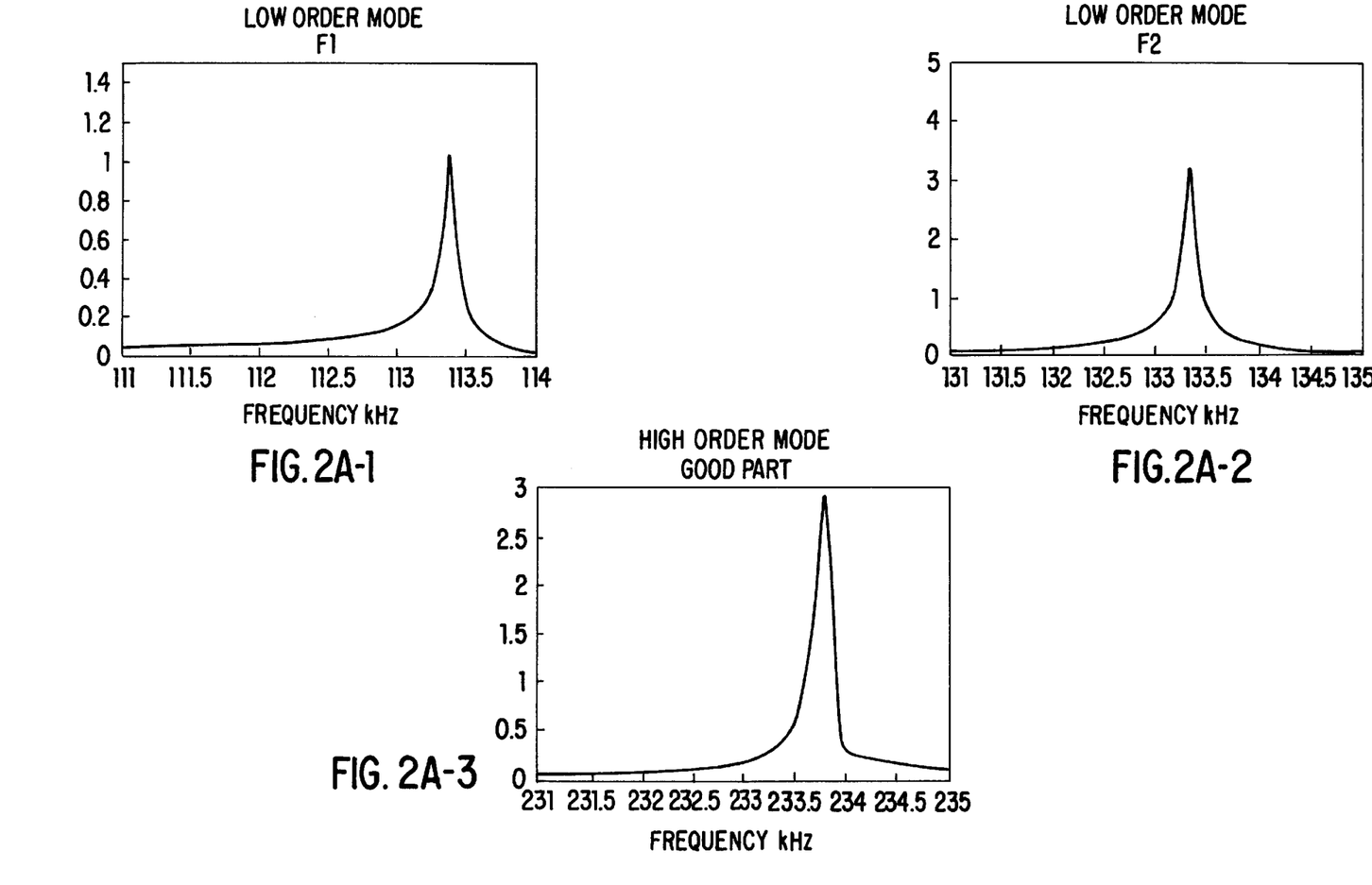
FIG. 2a illustrates the use of the technique disclosed here to compute the expected frequency of the diagnostic mode.
FIG. 2b shows the same calculation for a defective part, showing the splitting of the diagnostic mode.
Figure 2B:
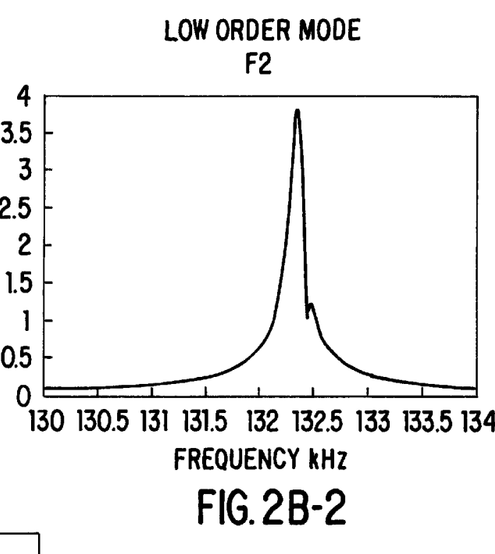
Figure 2B:
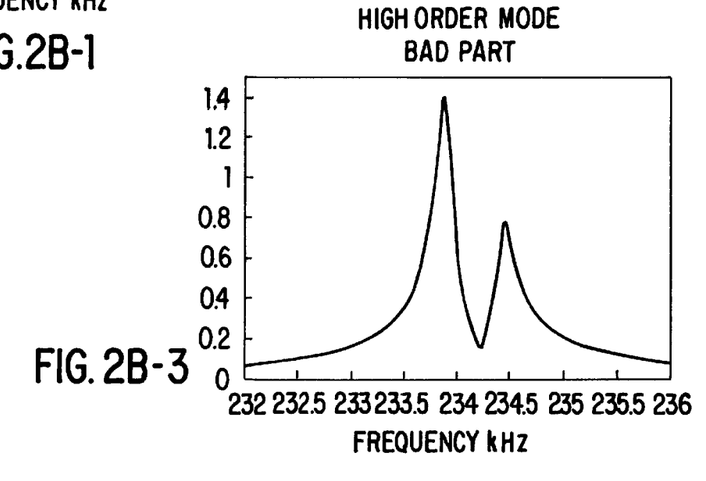
Figure 2B:
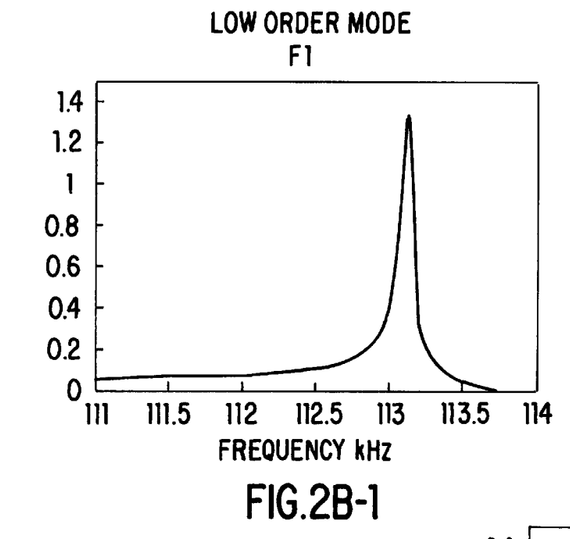

FIG. 2a illustrates the use of the technique disclosed here to compute the expected frequency of the diagnostic mode. The frequency of the two lower order modes $f_1$ and $f_2$, are measured using the first two windows. These frequencies are used with the equation:

$$f_h = A*f_1 + B*f_2 + C \qquad (13)$$

to compute the expected frequency for $f_h$. This can also be expressed in a general form with more terms as $$f_h = A*f_1 + B*f_2 + \ldots M*f_n + C$$

The lower end of the measurement window is set to be 0.5% below the expected frequency and the upper end is 1% above the expected frequency. Now the diagnostic mode is isolated in the measurement window and is easily detected. FIG. 2b shows the same calculation for a defective part, showing the splitting of the diagnostic mode.

Figure 3A:
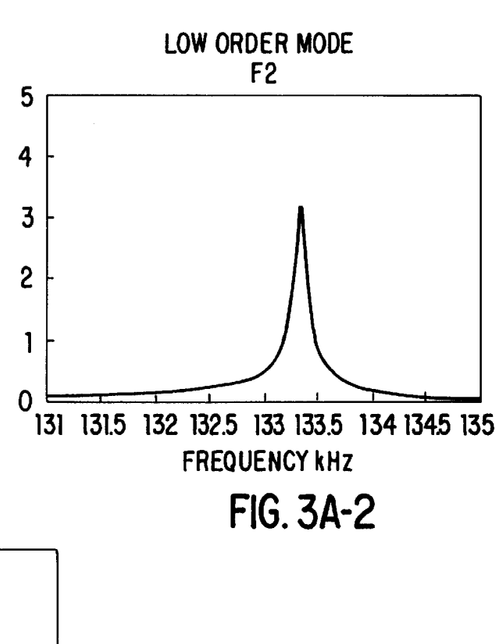
FIGS. 3a and 3b show the application of the expected frequency for testing using RUS shifts.
Figure 3A:
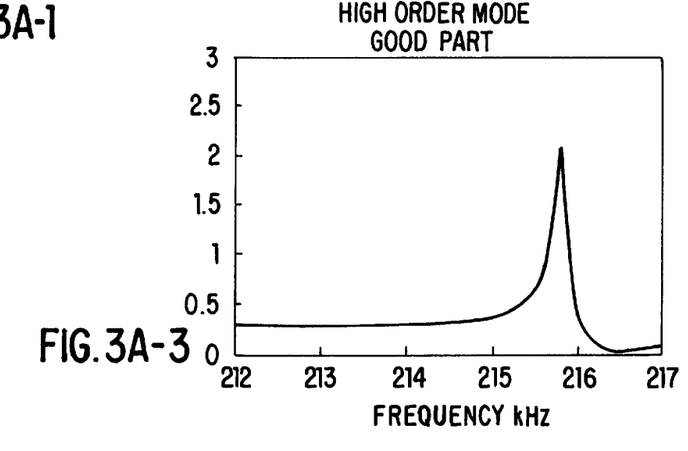
Figure 3A:
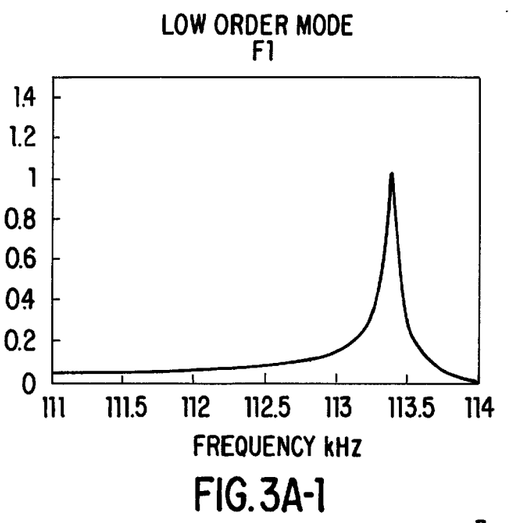
Figures 3B, 3B, 3B:
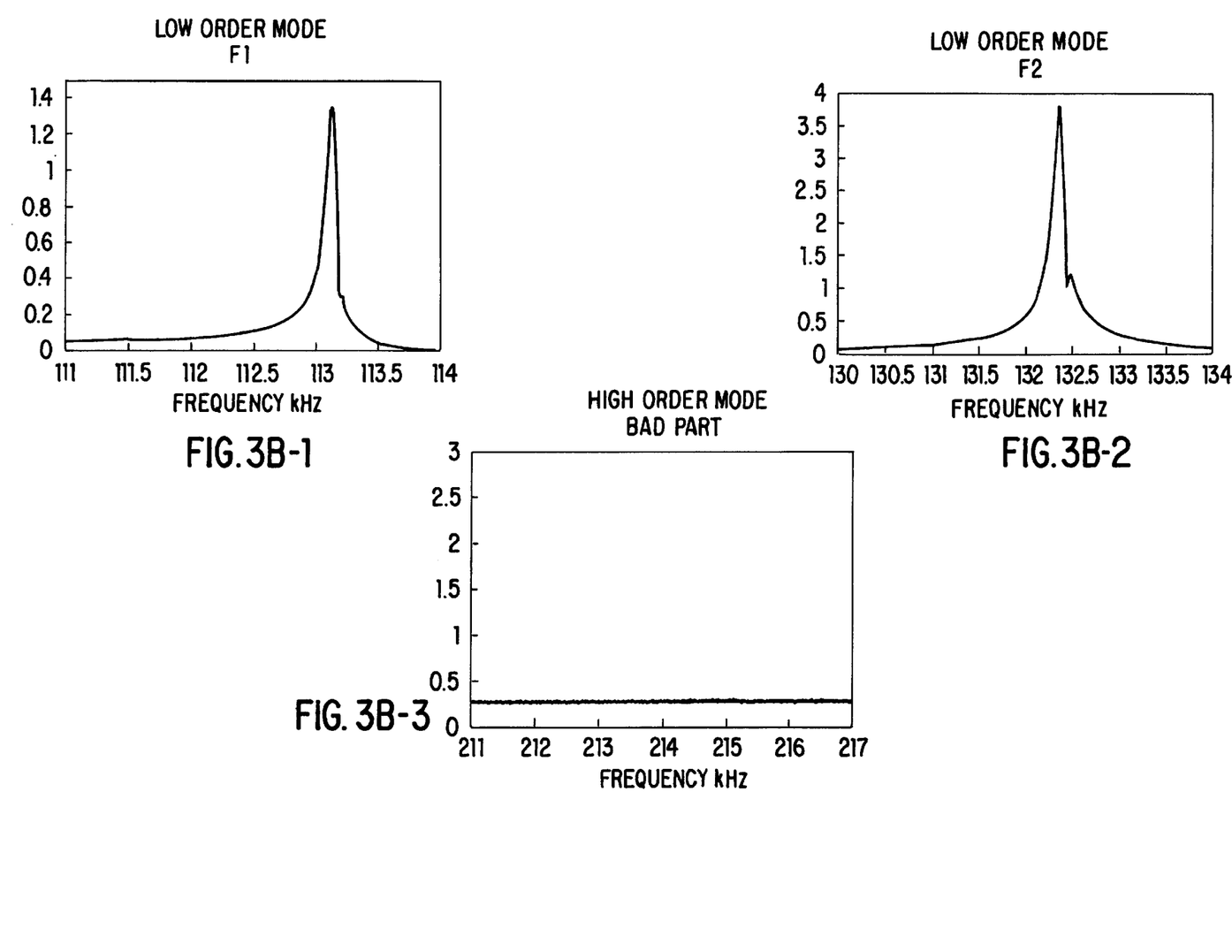

FIGS. 3a and 3b show the application of the expected frequency for testing using RUS shifts. In FIG. 3b the diagnostic mode has shifted out of the test window, so the part is defective. This example also shows another application of the expected frequency technique. Here, the diagnostic mode occurs at a lower frequency than one of the modes used to compute it. However, the diagnostic mode is adjacent to another unused mode, and it moves relative to that mode as the dimensions vary. The second mode, while it is at a higher frequency, is relatively isolated, and is always present. The expected frequency technique allows the diagnostic mode to be isolated so that its presence in the test window can be used to detect a defect.

Care must be exercised in selecting the low order modes so that at least one mode is used whose frequency correlates with each variable dimension. If two modes are used that each correlate only to the same dimension, then the relationships derived do not constitute simultaneous, independent equations and the solutions to the equations will not be meaningful. Most modes are driven primarily by a single dimension. For example, the first mode of a short cylinder (i.e., length to diameter ratio near one) is a torsional mode and it depends on length. For this type of mode the equation can be simplified to only two terms.

Empirical work has shown that short cuts can sometimes be used. For example, if one dimension does not vary significantly, it can be ignored. It has also been observed that other equations can be used to fit the frequency to dimension relationship over the limited range of interest. One such relationship is of the form:

$$f_h = A*f_m*f_n + B \qquad (14)$$

EXAMPLE 3

Practical application to RUS measurement of dimensions Using equations 2 and 3 (Example 1), the experimental procedure described above can measure the dimensions of a part type either during a production run or for statistical sampling. Again x+1 parts are required whose dimensions vary over the range of interest. These dimensions must be carefully measured. Similarly, x+1 resonant modes must be measured for each part. These modes must be selected so that at least one mode correlates to each dimension. This data is used to solve the simultaneous equations that relate the mode frequencies to the dimensions. The recommended procedure is to measure several modes for a large group of parts, (Such as, ten modes for 50 parts.) Each dimension of these parts is then correlated mathematically to the measured frequencies to select a mode that is highly correlated to that dimension. The resulting equations can be programmed into the RUS computer and the dimension of a part can be printed out as it is tested. A general mathematical statement of this example can be expressed as:

$$f_h = F(D_1, D_2, \ldots f_1, f_2 \ldots)$$

where D is a dimension, and f is frequency.

Figure 4:
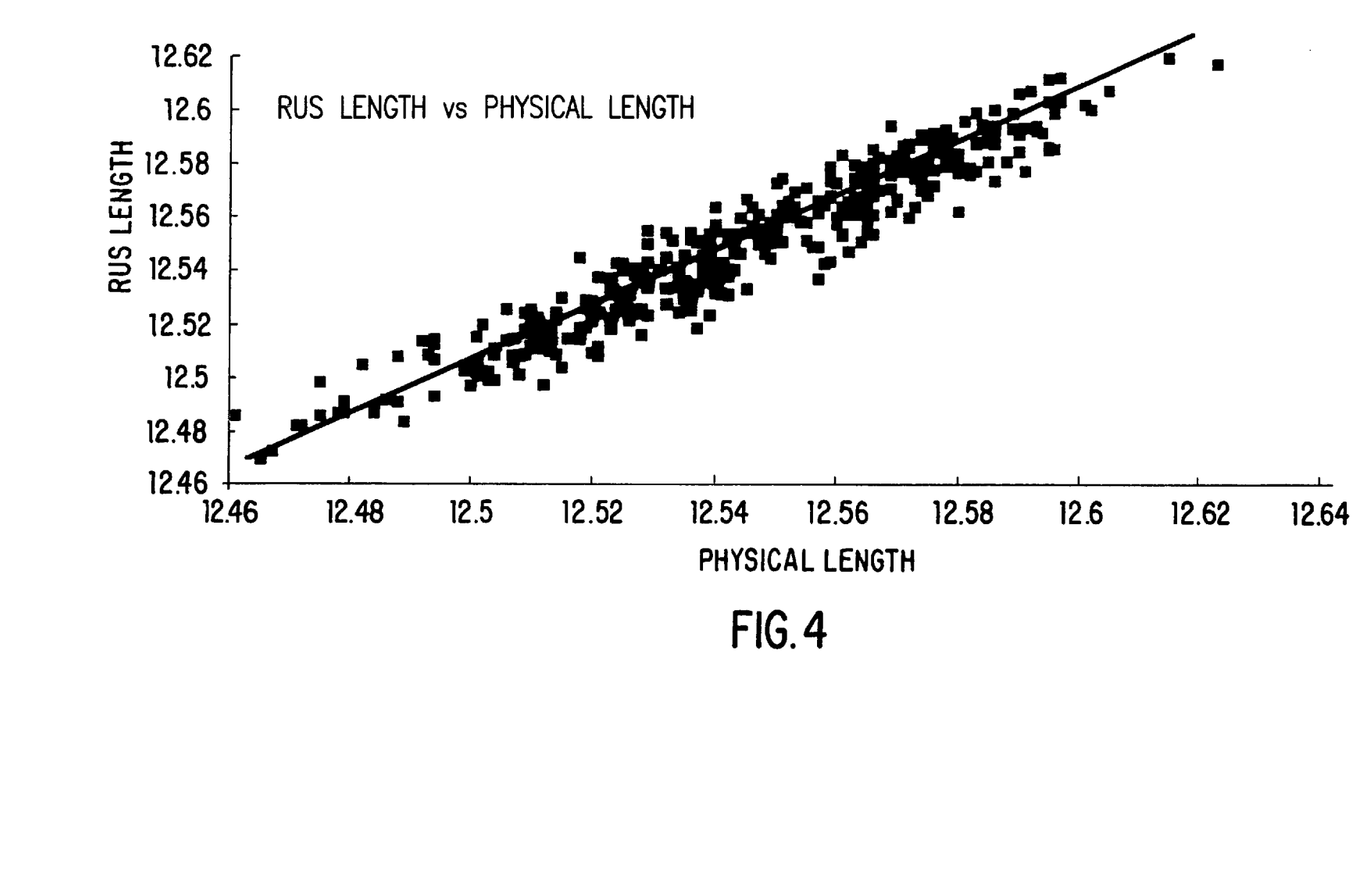
FIG. 4 is a graph comparing RUS measurement of length to the physical measurement.

Table 1 contains correlations between modes and dimensions for a sample manufactured part. This type of data provides the basis for selecting the modes to be used to measure dimensions. In cases where a mode can be identified that correlates to only one dimension, then the other modes can be ignored for measuring that dimension. FIG. 4 is a graph comparing RUS measurement of length to the physical measurement.

TABLE 1

CORRELATION OF MODES TO PHYSICAL PARAMETERS

| | MODE (kHz) | | | | | |
|---|---|---|---|---|---|---|
| | 115 | 135 | 205 | 210 | 215 | 235 |
| DIAMETER | 48% | 90% | 87% | 87% | −67% | −95% |
| HOLE | −58% | −20% | 0% | −20% | −40% | 10% |
| LENGTH | 98% | 30% | 4% | 35% | 78% | 2% |
| THICKNESS | 4% | 91% | 81% | 89% | −64% | −95% |
| WEIGHT | 21% | 98% | 87% | 96% | −49% | −97% |
| ASPECT RATIO | 49% | −60% | −74% | −55% | 95% | 79% |

EXAMPLE 4

High order SAW waves can be used for RUS detection of surface defects in non homogenous parts. U.S. Pat. No. 5,355,731 describes a technique for detecting surface defects in non-homogeneous parts such as ceramic ball bearings. That technique uses Surface Acoustic Waves (SAW) confined to the near surface of the part. The same RUS splits and shifts are used to detect the presence of a defect.

In order to confine the SAW to the surface, a high order diagnostic mode must be used. However, some of the physical parameters (dimensions and average density) that determine the precise frequency of the mode in a given part, can vary across a production run or from run to run. This causes the diagnostic mode to move relative to its neighboring modes. Since the SAW is always a high order mode, it lies in a spectral region of mode saturation. As a result it is difficult to track the diagnostic mode across a production run.

In this case the same general approach described above can be used to compute the expected frequency of the diagnostic mode. Actually, either of two related approaches can be used. The simpler approach is identical to that described in equation 13. Low order modes are correlated to the high order diagnostic mode to identify a set of low order modes that provide an accurate prediction of the expected frequency.

A second approach is applicable to parts that have a simple geometry that allows the resonant modes to be computed using an analytical model (a ball). Assume the density and the elastic constants are known well enough so that the model can accurately predict the modes. The dimensions vary across the production run. To test such a part the modes are first computed using typical values for dimensions. Then the RUS spectra is obtained. The computed and measured frequencies for selected low order modes are compared for a given part. The differences between the computed and measured frequencies are used to adjust determine the dimensions. Now, the real dimensions are known so the model can be used to compute the expected frequency of the diagnostic high order mode. The RUS shifts and splits can be used to detect surface defects.

EXAMPLE 5

This invention allows for adjusting for density variations in parts during RUS measurements. Density variations among a group of parts also present a challenge for using RUS. The resonant modes move with the inverse square root of the density. All of the modes move together, so this complicates the tracking of frequency shifts for both low order and high order modes. It also makes it difficult to track specific high order modes when using frequency shifts.

The technique disclosed here compensates for density effects based on the observation that the density variation affects all of the modes in the same direction, so the effect can be essentially eliminated by differencing similar modes. To illustrate this effect, rewrite equation 1 for a mode that depends only on length.

$$f_n = A_n * L + C_n \tag{15}$$

Now add a term to account for density variations. (Recalling the limitation that these equations only apply over the range of density variations encountered in typical production parts.)

$$f_n = A_n * L + C_n + 1/\sqrt{Ad} \tag{16}$$

where "d" is the density. Since d is generally not known and is difficult to measure for complex parts, the approach used for dimensional variations cannot be used directly. Note however, that if a second mode "$f_o$" that depends only on length is identified, then $$f_o = A_o * L + C_o + 1/\sqrt{Ad} \tag{17}$$

and if the difference of frequencies of the two modes is computed, $$f_n - f_o = Y * L + Z \tag{18}$$

where the constants have again been redefined to simplify the nomenclature. Note that equation 17 is independent of density. Given at least two good parts of known length, the approach described above can be used to solve for Y and Z. The result is an expression that measures length and is unaffected by density. The same approach can be used for any other dimension and for parameters that depend on dimensions, such as weight.

The accuracy of the measurement is degraded if the modes selected are not determined exclusively by the dimension of interest. The accuracy is also degraded if the variations are too large for the approximation of equation 1.

The same mode differencing approach can also be used to account for density variations when using RUS frequency shifts to detect defects. Refer to equation 18 which shows that the mode difference is independent of density. Chose modes $f_n$ and $f_o$ such that $f_n$ is a diagnostic mode for defects of interest and $f_o$ either does not vary with dimensions, or more practically, depends on a dimension that does not vary significantly for the part of interest. Then, the difference $f_n - f_o$ is inversely proportional to the frequency shift of $f_n$, and thus to the size of the defect. This assumes $f_n$ is larger than $f_o$. If the converse is true, then the difference is proportional to the size of the defect.

In practice it has been found that other mathematical functions can provide equal or superior results. For example, the expression $$f_n/f_o = Y * L + Z \tag{19}$$

which uses the ratio of the modes, sometimes provides a better fit.

EXAMPLE 6

Location of high order RUS modes when both dimensions and density vary is possible by this example. Computing the expected frequency across groups of parts whose density and dimensions both vary (different batches of ceramic parts, for example) has been accomplished by the technique disclosed here.

Figure 5:
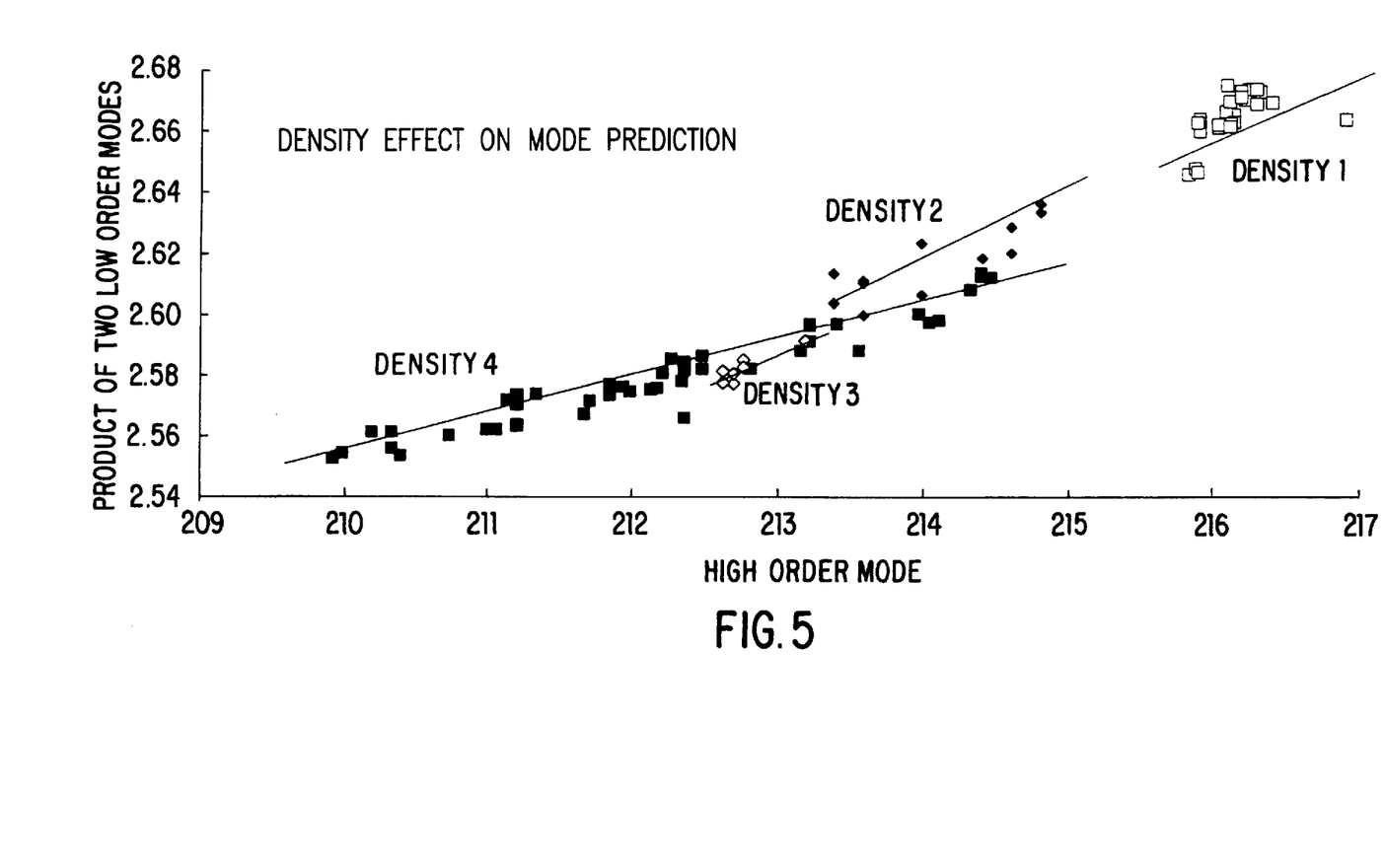
FIG. 5 is a graph comparing a high order mode to the product of two lower order modes.

The problem can be visualized as shown in FIG. 5 which plots expected frequency for a high order mode vs the product of two other modes using equation 12. Data is provided for a range of dimensions for parts of one density and for average sized parts at 2 other densities. Each density establishes a unique line relating the variables. The density is unknown and the relationships are too complex to derive an adjustment that would make the relationship independent of density.

It has been determined that the expected frequency can be computed with acceptable accuracy (about 99%) by fitting equation 12 to the entire range of data. This can be done with a standard best fit algorithm, but care must be taken to assure that equal weight is given to both ends of the range of parts.

We claim:

1. A method of RUS (Resonant Ultrasound Spectroscopy) measurement of an object comprising the steps of:

measuring the object frequency response by RUS at low order frequency modes $f_n$;

computing at least one higher order mode frequency ($f_h$) as a function of said measurement by RUS at lower order modes; and measuring frequency response of said object by RUS at said higher order mode frequency ($f_h$); and wherein said measuring of frequency response by RUS at low order frequency modes ($f_1, f_2 \ldots$) are any function of the object dimensions (D) and wherein response frequencies ($f_h$) can be expressed as:

$$f_h = F(D_1, D_2, \ldots f_1, f_2, \ldots)$$

where F is the general mathematical term denoting a function of.

2. A method of RUS (Resonant Ultrasound Spectroscopy) measurement comprising the steps of:

measuring resonant frequencies ($f_n$) of a plurality of parts having no defects which affect measured resonant frequencies ($f_n$) at low-order frequency modes;

determining relationships between the measured resonant frequencies ($f_n$), and dimensions of the parts having no defects;

predicting expected frequency of a high-frequency ($f_h$) resonant mode by calculating coefficients of said determined relationships from said measured resonant frequencies ($f_o$) at low-order frequency modes;

measuring by RUS the response of an unknown part at said high-frequency ($f_h$) mode;

accepting and rejecting said unknown part based upon criterion applied to said measured RUS response at the high-frequency ($f_h$) mode; and wherein one of said relationships is in the mathematical form of:

$$f_h = F(D_1, D_2, \ldots f_1, f_2 \ldots)$$

where D is a dimension, f is frequency and F is the mathematical term denoting any function of.

3. A method in accordance with claim 2 wherein said relationships are measurements in units of length.

4. A method in accordance with claim 2 wherein said relationships are approximated dimensional relationships.

5. A method in accordance with claim 2 wherein the plurality of parts measured is a number x+1, where x is a number of dimensional dependent terms in said relationships.

6. The method in accordance with claim 2 wherein the plurality of parts is a number of parts which is greater than x+1 where x is a number of dimensional dependent terms in said relationships, and determining said coefficients is by a best fit technique.

7. A method in accordance with claim 2 wherein the step of measuring by RUS applies frequencies in a band of frequencies including said expected frequency of a high-frequency ($f_h$).

8. A method in accordance with claim 7 wherein said band of frequencies is within 3% of said expected frequency.

9. A method in accordance with claim 2 wherein one of said relationships is a function in a mathematical form of:

$$f_h = A * f_1 + B * f_2 + \ldots M * f_n + C;$$

wherein A, B, and M are coefficients and C is a constant; and wherein $f_1$ and $f_2$, and $f_n$ are measured resonant frequencies.

10. A method in accordance with claim 2 wherein one of said relationships is in the mathematical form of:

$$f_h = a * f_1 * f_2 + c;$$

wherein a is a coefficient and c is a constant; and wherein $f_1$ and $f_2$ are measured resonant frequencies.

11. The method in accordance with claim 1 wherein said RUS is in a frequency band which allows shifts in frequency to be identified.

12. The method in accordance with claim 1 wherein said RUS is at in a frequency band which will allow detection of splits in resonant peak of said higher order mode frequency.

13. The method in accordance with claim 1 wherein said dimensions are in units selected from the group consisting of length and mass.

* * * * *